(12) United States Patent
Schneider et al.

(10) Patent No.: US 7,820,347 B1
(45) Date of Patent: Oct. 26, 2010

(54) CONVERSION OF SALT HALIDES TO NITRATE SALTS

(75) Inventors: Stefan Schneider, Palmdale, CA (US); Tommy W. Hawkins, Lancaster, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 80 days.

(21) Appl. No.: 12/075,288

(22) Filed: Jan. 31, 2008

Related U.S. Application Data

(60) Provisional application No. 60/900,308, filed on Feb. 6, 2007.

(51) Int. Cl.
*G03G 15/02* (2006.01)
*C07D 249/00* (2006.01)

(52) U.S. Cl. .................................. 430/58.5; 548/262.2
(58) Field of Classification Search ............. 548/262.2, 548/264.8; 430/58.5
See application file for complete search history.

(56) References Cited

U.S. PATENT DOCUMENTS 6,509,473 B1 * 1/2003 Drake ...................... 548/262.2

* cited by examiner

*Primary Examiner*—Susannah Chung
(74) *Attorney, Agent, or Firm*—AFMCLO/JAZ; Thomas C. Stover

(57) ABSTRACT

Methods of preparing heterocyclic triazolium-based nitrate salts by a streamlined process are provided. Such salts offer energetic performance as well as pharmaceutical potential.

2 Claims, No Drawings

CONVERSION OF SALT HALIDES TO NITRATE SALTS

CROSS-REFERENCE TO RELATED PATENT APPLICATIONS

This Application relates to a provisional patent application Ser. No. 60/900,308, entitled Conversion of a Salt Halide to a Nitrate Salt, by the same inventors, filed in the USPTO on 6 Feb. 2007.

STATEMENT OF GOVERNMENT INTEREST

The invention described herein may be manufactured and used by or for the Government for governmental purposes without the payment of any royalty thereon.

FIELD OF THE INVENTION

This invention relates to preparation of nitrate salts, particularly heterocyclic nitrate salts.

BACKGROUND OF THE INVENTION

An alkylated triazolium based nitrate salt has potential in propulsion and/or explosives applications. One of the current, major drawbacks in commercializing these so called ionic liquids or low melting salts is the use of silver salts as ion exchange agents. Use of silver introduces high cost, along with light sensitivity and residual contamination. The elimination of silver salts would decrease the cost of production and virtually eliminate heavy metal waste and contamination.

Accordingly, there is need and market for preparing the above family of salts without the need for silver salts therewith in a more streamlined process of reduced costs.

There has now been developed an efficient method to produce the above family of salts free from the use of silver salts therewith.

SUMMARY OF THE INVENTION

Broadly, the present invention provides a method for preparing isomerically pure, alkylated, triazolium-based, nitrate salts, including, reacting substituted amino 1,2,4-triazolium and 1,2,3-triazolium halides with dinitrogen tetroxide.

The invention further provides salts formed by the above method including alkylated, triazolium-based, nitrate salts comprising 1-hydroxyethyl-1,2,4-triazolium nitrate, 1-propionitrile-1,2,4-triazolium nitrate, 1-acetonitrile-1,2,4-triazolium nitrate or 1-propyl-1,2,3-triazolium nitrate or combinations thereof.

These inventive compounds are also useful in the preparation of pharmaceutical and agricultural agents, also as highly energetic compounds for explosives, propellants and gas-generating compositions and formulations.

DESCRIPTION OF PREFERRED EMBODIMENTS

The following description serves to illustrate the versatility of the present invention.

Three 1-R-4-amino-1,2,4-triazolium bromides (R=hydroxyethyl, propionitrile, acetonitrile) and 1-amino-3-propyl-1,2,3-triazolium bromide were chosen for an initial evaluation of the process. In a typical experiment, a frozen mixture of a triazolium halide in excess $N_2O_4$ was allowed to slowly warm from −196° C. ($LN_2$) to ambient temperature. Preliminary investigations of the products showed that in all four cases nitrate salts were produced but that the cations were also affected. The actual composition of the products was only revealed after detailed studies by mass balance, Raman, IR, multinuclear NMR spectroscopy, DSC, elemental and X-ray analysis. Besides a halide/nitrate exchange the reactions in neat $N_2O_4$ also caused cleavage of the amino group attached to the heterocycles. The final salts represent simple alkylated 1,2,4- and 1,2,3-triazolium nitrates. These results are notable because a regiospecific alkylation of simple triazoles has always provided a synthetic challenge. Generally, ratios of the two possible isomers vary between 90 to 10 and 70 to 30 depending on the alkylating agent and conditions.

The following examples serve to illustrate the method of the present invention and should not be construed in limitation thereof.

Example 1

1-hydroxyethyl-1,2,4-triazolium nitrate. 0.44 g (2.11 mmol) of 1-hydroxyethyl-4-amino-1,2,4-triazolium bromide were added to a 20 mL glass reaction vessel equipped with a Kontes Teflon© valve. The vessel was connected to a glass vacuum line and evacuated. 4.01 g (43.61 mmol) dinitrogen-tetroxide were condensed on top of the 1-hydroxyethyl-4-amino-1,2,4-triazolium bromide at −196° C. The frozen reaction mixture was allowed to warm to room temperature. After 10-15 min at ambient temperature all volatiles were removed in a dynamic vacuum. The remaining residue was dissolved in methanol and layered with diethylether. The product crystallized out over night, was filtered, washed with diethylether and dried in a dynamic vacuum. The material was identified by $^1H$, $^{13}C$, $^{14}N$, NMR spectroscopy, by DSC, elemental and X-ray analysis.

Example 2

1-propionitrile-1,2,4-triazolium nitrate. 0.28 g (1.28 mmol) of 1-propionitrile-4-amino-1,2,4-triazolium bromide were added to a 20 mL glass reaction vessel equipped with a Kontes Teflon© valve. The vessel was connected to a glass vacuum line and evacuated. 2.73 g (29.71 mmol) dinitrogen-tetroxide were condensed on top of the 1-propionitrile-4-amino-1,2,4-triazolium bromide at −196° C. The frozen reaction mixture was allowed to warm to room temperature. After 10-15 min at ambient temperature all volatiles were removed in a dynamic vacuum. The remaining residue was dissolved in methanol and layered with diethylether. The product crystallized out over night, was filtered, washed with diethylether and dried in a dynamic vacuum. The material was identified by 1H, $^{13}C$, $^{14}N$, NMR spectroscopy, by DSC, and X-ray analysis.

Example 3

1-acetonitrile-1,2,4-triazolium nitrate. 0.35 g (1.70 mmol) of 1-acetonitrile-4-amino-1,2,4-triazolium bromide were added to a 20 mL glass reaction vessel equipped with a Kontes Teflon© valve. The vessel was connected to a glass vacuum line and evacuated. 3.13 g (34.06 mmol) dinitrogentetroxide were condensed on top of the 1-acetonitrile-4-amino-1,2,4-triazolium bromide at −196° C. The frozen reaction mixture was allowed to warm to room temperature. After 10-15 min at ambient temperature all volatiles were removed in a dynamic vacuum. The remaining residue was dissolved in methanol and layered with diethylether. The product crystallized out over night, was filtered, washed with diethylether and dried in a dynamic vacuum. The material was identified by $^1H$, $^{13}C$, $^{14}N$, NMR spectroscopy, by DSC, and X-ray analysis.

Example 4

1-amino-3-propyl-1,2,3-triazolium nitrate. 0.38 g (1.85 mmol) of 1-amino-3-propyl-1,2,3-triazolium bromide were added to a 20 mL glass reaction vessel equipped with a Kontes Teflon© valve. The vessel was connected to a glass vacuum line and evacuated. 3.29 g (35.7 mmol) dinitrogentetroxide were condensed on top of the 1-amino-3-propyl-1,2,3-triazolium bromide at −196° C. The frozen reaction mixture was allowed to warm to room temperature. After 10-15 rain at ambient temperature all volatiles were removed in a dynamic vacuum. The remaining residue was dissolved in methanol and layered with diethylether. In this case no crystallization occurred. Upon pumping off the volatiles in a dynamic vacuum a solid was left behind. The mp was determined by DSC to +36.5° C. The material was identified by $^1$H, $^{13}$C, $^{14}$N, NMR spectroscopy, and by DSC analysis.

The present invention thus provides an effective method for making the above nitrate salts through a facile synthesis route in high yields and purity.

Accordingly, it can be seen that amino-triazolium halide salts, in $N_2O_4$, form isomerically pure compounds in a single step reaction. That is, a one step conversion (without the use of silver salts and without residual contamination) of a substituted amino-triazolium heterocyclic salt halide to the corresponding substituted triazolium nitrate, is described.

The above nitrate salts of the invention have potential in propulsion and/or explosive applications. The above salts offer the potential for improved propulsion performance and explosive power. Also the performance, cost and safety property aspects of these new ingredients can find use in commercial propellant and/or explosive applications.

Further, this approach of making isomerically pure, alkylated, triazolium salts could well be of interest to the pharmaceutical industry. That is, the production of isomer-pure alkylated triazoles is also of use in the production of certain pharmaceuticals.

What is claimed is:

1. A method for preparing isomerically pure, alkylated, triazolium-based, nitrate salts of the formula,

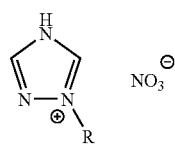

1-Substituted 1, 2, 4-triazolium nitrates comprising, reacting substituted amino 1,2,4 triazolium halides with dinitrogen tetroxide as follows:

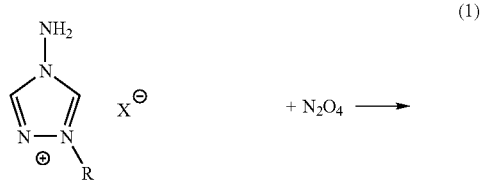

1-Substituted 4-amino-1,2,4-triazolium halides

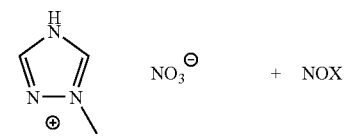

1-Substituted 1,2,4-triazolium nitrates where X is halide and R is alkyl, hydroxyethyl, propionitrile or acetonitrile, R is alkyl, hydroxyethyl, propionitrile or acetonitrile.

2. An alkylated, triazolium-based, nitrate salts of the formula,

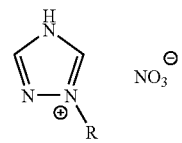

1-Substituted 1, 2, 4-triazolium nitrates where R is alkyl, hydroxyethyl, propionitrile or acetonitrile, consisting of 1-hydroxyethyl-1,2,4-triazolium nitrate, 1-propionitrile-1,2,4-triazolium nitrate, or 1-acetonitrile-1,2,4-triazolium nitrate.

\* \* \* \* \*